United States Patent [19]

Recchuite

[11] 4,166,796

[45] Sep. 4, 1979

[54] COMPOSITION COMPRISING A COSULFURIZED BLEND OF LARD OIL AND AN OLEFIN

[75] Inventor: Alexander D. Recchuite, Boothwyn, Pa.

[73] Assignee: Suntech, Inc., Philadelphia, Pa.

[21] Appl. No.: 905,909

[22] Filed: May 15, 1978

Related U.S. Application Data

[63] Continuation of Ser. No. 220,399, Jan. 24, 1972, which is a continuation-in-part of Ser. No. 135,466, Apr. 19, 1971, abandoned.

[51] Int. Cl.$^2$ .................... C10M 1/38; C10M 5/22; C09B 49/00; C07G 17/00
[52] U.S. Cl. .................... 252/48.6; 260/125; 260/139; 260/399
[58] Field of Search ............... 252/48.6; 260/125, 399, 260/139

[56] References Cited

U.S. PATENT DOCUMENTS

| | | | |
|---|---|---|---|
| 3,316,237 | 4/1967 | Imparato et al. | 260/139 |
| 3,455,896 | 7/1969 | Den Herder et al. | 252/48.6 |
| 3,825,495 | 7/1974 | Newingham et al. | 252/48.6 |

*Primary Examiner*—Irving Vaughn

*Attorney, Agent, or Firm*—J. Edward Hess; Donald R. Johnson; Paul Lipsitz

[57] ABSTRACT

Process of sulfurizing a blend of 90 to 50 and preferably 88 to 70 parts by volume of triglyceride such as lard oil and 10 to 50 and preferably 12 to 30 parts by volume of an ethylenically unsaturated hydrocarbon contaning 2 to 24 carbon atoms. The sulfurization is carried out using elemental sulfur. Simultaneous sulfurization and chlorination may be effected by reacting with sulfur monochloride. Phosphosulfurization may also be carried out by addition of small amounts of a phosphorus sulfide to the sulfurized blend followed by heating at 180° F. to 250° F. for from 30 minutes to 10 hours to effect phosphosulfurization. The sulfurization or phosphosulfurization involves reacting at from 330° F. to 445° F. for 20 minutes to 10 hours followed by blowing with a gas at from 125° F. to 250° F. for 30 minutes to 20 hours to remove hydrogen sulfide. The simultaneous sulfurization and chlorination reaction is carried out at from 90° F. to 280° F. for from 20 minutes to 10 hours followed by blowing with a gas at from 125° F. to 250° F. for 30 minutes to 20 hours. The sulfurized oils contain from 7.5 to 25 weight percent sulfur as based on the blend of olefin and triglyceride.

15 Claims, No Drawings

COMPOSITION COMPRISING A COSULFURIZED BLEND OF LARD OIL AND AN OLEFIN

CROSS REFERENCE TO RELATED APPLICATIONS

This application is a continuation of 220,399 filed Jan. 24, 1972 by Alexander D. Recchuite which in turn is a continuation-in-part of United States application Ser. No. 135,466 filed Apr. 19, 1971 by Alexander D. Recchuite (now abandoned) which in turn is related to United States application Ser. No. 116,985 (now U.S. Pat. No. 3,825,495) filed on Feb. 19, 1971 by Thomas D. Newingham, Alexander D. Recchuite, John Q. Griffith, III and Marcus W. Haseltine, Jr., and entitled "Lubricant for Controlled-Slip Differential".

BACKGROUND OF THE INVENTION

In the past, sulfurized sperm oil has been used as an additive such as for friction modifiers in many lubricant formulations such as in gear oils, worm and spur gears, automatic transmission fluids, way lubricants, Permawick lubes for sintered bronze or sintered babbit bearings, and as a metal-working oil additive. Sperm oil has now become restricted and the present invention is directed to a replacement for sulfurized sperm oil. Sulfurized olefins alone do not have the lubricity necessary for many applications as is indicated by their high stick/slip ratios. Sulfurized naturally occurring triglycerides such as lard oil do not have adequate solubility in paraffinic base oils. It has now been found that by sulfurizing a blend of a triglyceride and an ethylenically unsaturated hydrocarbon and preferably an olefin together a material is obtained which has good lubricity and is soluble in paraffinic base lube stocks. When the olefin and triglyceride are sulfurized separately and then blended together, a different product is obtained and the blend of the separately sulfurized oils comes out of solution in paraffinic base lubes. When one or the other of the triglyceride and olefin are separately sulfurized and then blended with the unsulfurized component and reexposed to sulfurization conditions, a different product is also obtained.

SUMMARY OF THE INVENTION

The present invention involves blending from 90 to 50 and preferably from 88 to 70 parts by volume of triglyceride and from 10 to 50 and preferably from 12 to 30 parts by volume of an olefin, sulfurizing the blend and then blowing the sulfurized blend with a gas to remove hydrogen sulfide. The triglyceride and olefin generally are blended together at from 65° F. to 340° F. and the sulfur added while the blend is within this temperature range. The naturally occurring triglycerides are preferred because of their low price and ready availability. The preferred triglyceride for use herein is lard oil. The preferred commercial lard oil generally is described as winter grade lard oil. Lard oils suitable for use in this invention are defined in Table I.

TABLE 1

| Properties | Preferred Lard Oils | Suitable Lard Oils |
| --- | --- | --- |
| Free Fatty Acids as Oleic | 2–5 | 12–20% |
| Saponification Number | 192–198 | 192–198 |
| Pour Point (ASTM) | 35–45 | 35–50 |
| Viscosity SUS @ 10° F. | 200–210 | 200–210 |
| Melting Point | 65–75 | 65–75 |

TABLE 1-continued

| Properties | Preferred Lard Oils | Suitable Lard Oils |
| --- | --- | --- |
| Sp. Gr. 25° C. | 0.910–0.915 | 0.910–0.915 |
| Iodine Number | 60–75 | 60–75 |

The principal difference between the less preferred grades such as No. 1. lard oil and the preferred grade is in the amount of saturates present which reduce the solubility of the product. The preferred specifications as reported in Table I include grades which are superior to extra winter strained lard oil as well as winter strained lard oil. Numerous other naturally occurring triglycerides are suitable for use in the present invention. The fatty acid portion of the triglycerides will generally consist essentially of acids containing from 9 to 22 carbon atoms. At least about 45 mole percent of the fatty acid moiety present in the triglyceride will contain at least one ethylenically unsaturated carbon-carbon double bond. Such suitable triglycerides include but are not limited to menhaden oil, whale oil (not sperm oil), soybean oil, cottonseed oil, safflower oil, linseed oil, rapeseed oil, sunflower oil, peanut oil and tall oil. The fatty acid portion of the triglyceride should be a hydrocarbon except for the carboxyl group. Thus, triglycerides such as castor oil wherein the acids contain a hydroxyl group are excluded. Such triglycerides are undesirable because of their poor solubility in oil. The olefins suitable for use in the present invention generally contain from 2 to 24 carbon atoms. For convenience in performing the process of the present invention in unpressurized open vessels, the olefin should contain at least 12 and preferably 15 carbon atoms in order to prevent loss thereof from boil off as the reaction mixture is heated. The olefin may be straight chain or branched. Also suitable are any hydrocarbon containing one ethylenically unsaturated carbon-carbon double bond and one aromatic or cycloaliphatic ring. Multiple ring hydrocarbons and di or tridouble bond containing hydrocarbons do not give as oil soluble a product as is desired. The true olefins are preferred. The double bond should not be in a ring or reduced solubility of the product in paraffinic oils will be observed. Thus the suitable unsaturated hydrocarbons have the structure

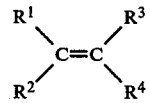

where $R^1$, $R^2$ and $R^3$ are either hydrogen or alkyl and $R^4$ is hydrogen, alkyl, aryl, cycloalkyl or alkaryl. Generally the α-olefins give the best properties in the final product. As far as final product properties are concerned, α-olefins containing from 8 to 12 carbon atoms are preferred. When using a normally gaseous unsaturated hydrocarbon the volume percent present is calculated from the apparent density of such unsaturated hydrocarbon in a normally liquid hydrocarbon.

The amount of sulfur generally varies from 7.5 to 25 percent by weight as based on the blend of triglyceride and olefin. When an inactive sulfurized product is desired, from 7.5 to 11.0 weight percent sulfur as based on the blend of triglyceride and olefin is used. Under the conditions used, this amount of sulfur will become chemically bonded almost entirely in an inactive form.

The resultant product containing 7.5 to 11 weight percent sulfur as based on the blend of triglyceride and olefin is useful as a friction modifier for many applications as well as a metal-working oil.

When sulfurized oils are used as metal-working oils, often it is desirable that they contain a relatively large amount of sulfur because it is the sulfur itself which is the most important ingredient due to its function as an antiweld agent. Generally in such metal-working oils from 16 to 25 weight percent sulfur should be present. The sulfur present above the 11 weight percent level will be in the active form. The amount of sulfur in a given sample of oil is readily determined by X-ray fluorescense. After the amount of total sulfur is determined, 100 g. of the oil sample and 20 g. of copper powder are placed in a tall 250 ml. beaker set up on a hot plate and equipped with a thermometer and an auger stirrer operated at 1750 rpm. The sample is heated to 350° F. within a 5 minute period and maintained at 350° F.±5° F. for one hour after which it is cooled and filtered through filter paper to remove the copper powder. The sulfur content of the sample is again determined by X-ray fluorescence which is the inactive sulfur. The loss of sulfur (total minus inactive sulfur) is the amount of active sulfur in the original.

The amount of active sulfur in a sulfurized oil being used as a friction modifier should be less than 2.5 wt. percent. Generally the friction modifiers of the present invention containing 7.5–11% by weight total sulfur contain from 1 to 2% by weight active sulfur. The sulfurized metal-working oil additives of the present invention which contain from 16–25% by weight total sulfur generally contain from 5–18% by weight active sulfur. Generally the sulfur is added to the triglyceride-olefin blend over a period of 1 to 60 minutes while the blend is maintained at from 250° F. to 330° F. with constant stirring. The temperature is not particularly critical, the 250° F. represents the softening point of the sulfur and the 330° F. represents the flash point of the triglyceride-olefin blend when the olefin is a blend containing 15-20 carbon atoms. The high sulfur oils of the present invention are soluble in paraffinic oils, as illustrated by testing a 10 g. sample in 100 g. of oil at 36° F. for 16 hours and room temperature for one week. In contrast, commercial highly sulfurized triglycerides such as sulfurized lard oil and commercial highly sulfurized sperm oil separate from paraffinic oils after testing at the above specified conditions. Generally for metal-working oil use the sulfurized oil is dissolved in the paraffinic oil to form a 5–20% by volume solution of sulfurized oil in the paraffinic oil. When using $S_2Cl_2$ which is normally a liquid it may be added to the triglyceride-olefin blend at ambient temperature followed by reacting at over 90° F. due to its increased chemical activity as compared with elemental sulfur. When phosphosulfurizing consulfurized triglyceride-olefin blend generally from 0.5 to 3% by weight of phosphorus is used. Therefore a phosphorus sulfide plus sulfur is used to provide the required amounts of phosphorus and sulfur. The preferred phosphorus sulfide is phosphorus sesquisulfide. The reaction conditions and times used in phosphosulfurization are from 180° F. to 250° F. for from 30 minutes to 10 hours followed by blowing with a gas at 125° F. to 250° F. for about 30 minutes to two hours.

After addition of sulfur the mixture is heated. Where it is desired to maximize the amount of active sulfur present, a temperature as low as 330° F. may be used. The sulfurized oils of the present invention have flash points of about 445° F. and this is therefore the maximum temperature that should be used in the heat step. While pressure apparatus could be used if desired which would raise the maximum possible temperature, the reaction is most readily carried out at atmospheric pressure due to economic considerations. Furthermore little advantage is obtained in using a temperature above 445° F. With the formulations where a minimum of active sulfur is desired, the heating should be carried out at greater than 365° F. In the case of the formulations where the presence of high amounts of active sulfur are desired, the heating should not be done at over 345° F. Generally the heating is carried out for from 20 minutes to 10 hours.

After the heating step the sulfurized oil is blown with a gas to remove $H_2S$. Any gas may be used which dissolves $H_2S$ and does not significantly react with the sulfurized oil. Suitable gases include air, nitrogen, carbon dioxide and gaseous perhalogenated hydrocarbons. Air is preferred for obvious economic considerations. The blowing is most simply carried out by bubbling the gas through the sulfurized oil. Alternatively the oil may be sprayed into the gas or a falling curtain of the oil in the gas may be used. Generally the blowing is carried out at from 125° F. to 250° F.

The sulfur may be added either as elemental sulfur or sulfur monochloride ($S_2Cl_2$). The elemental sulfur is usually preferred for the low sulfur (7.5–11 wt. %) oils but $S_2Cl_2$ is often preferred for the metal-working oil applications because the chlorine also reacts with the oil and serves to improve the antiweld characteristics of the product. When using $S_2Cl_2$ the temperature should be maintained below 280° F. (the boiling point of $S_2Cl_2$) unless a pressure apparatus is being used for maximum retention of chlorine.

The products of the present invention possess properties not possessed by either sulfurized triglyceride or sulfurized olefins or blends of separately sulfurized triglyceride and separately sulfurized olefins. The sulfurized triglyceride suffers from lack of compatibility with paraffinic lubes. The sulfurized olefins do not have adequate lubricity as evidenced by their poor stick/slip ratios. (Static friction/dynamic friction when used as a lube additive). The combination of stick/slip and compatibility properties are particularly important in automatic transmission fluids and limited slip differential fluids. Automatic transmission fluids normally contain 75–98% by. vol. of a paraffinic base oil and from 2–25% by vol. additives. The additives are necessary because no oil alone has all of the viscosity, flash point, foaming and lubricity, etc. properties usually desired in an automatic transmission fluid. To achieve these properties the oil must be fortified with various additives. Usually a plurality of additives are used, each specific additive being designed to imrpove one specific property of the hydrocarbon oil. A composition adapted for use as an automatic transmission fluid will normally have a viscosity of at least 49.0 SUS @ 210° F. Moreover the viscosity of the fluid must remain substantially constant during the use of the fluid. It will usually have a viscosity of at least 46.5 SUS @ 210° F. after being used in a car which is repeatedly accelerated sufficiently to bring the temperature of the fluid to 300° F. The fluid should have a flash point of at least 320° F. as determined by ASTM D-92. Further descriptions of typical automatic transmission fluid properties are fully set forth in U.S. Pat. No. 3,388,068, issued June 11, 1968, Thoman D.

Newingham and U.S. Pat. No. 3,017,361, issued Jan. 16, 1962, John R. Morris et al. The sulfurized oils of the present invention are useful as friction modifiers in such fluids to reduce the static friction more than the dynamic fraction. Generally the sulfurized oils of the present invention are used at from 1–5% by vol. of the overall fluid. A typical automatic transmission fluid might have the following composition: 82.7% by vol. solvent-refined paraffinic lube having a viscosity of 40.3 SUS @ 210° F. and a viscosity index of 101, 3% by vol. of the sulfurized oil of Example X, 0.5% by vol. of zinc dialkyldithiophosphonate, 0.5% by vol. of 4,4'-methylenebis(2,6-di-tert-butylphenol), 0.3% by vol. barium phosphonate, 1% by vol. of over-based barium sulfonate and 15% by vol. of hydrogenated naphthenic lube as a seal swell agent.

DESCRIPTION OF THE PREFERRED EMBODIMENTS

EXAMPLE I

Three hundred grams of winter strained lard oil are blended with 300 g. of $\alpha$-olefins in a 5 L kettle equipped with a vibromixer. The $\alpha$-olefins are a blend of predominantly straight chain mono-$\alpha$-olefins containing from 15 to 20 carbon atoms. The mixture is heated to 250° F. and the vibromixer is operated at maximum speed. These conditions are maintained and 60 g. of sulfur are added over a period of a few minutes. The temperature is raised to 375° F. and held at that temperature for two hours. The temperature is reduced to 200° F. and air is bubbled through the stirred mixture for one hour by means of a glass tube at a moderate rate below that at which splashing and agitation take place to remove hydrogen sulfide. The resulting sulfurized oil is analyzed and found to contain 8.7% sulfur as based on the total composition. A 10 g. portion of the sulfurized oil is dissolved in 100 g. of Oil "A". Oil "A" is a commercial solvent-refined paraffinic base oil having a viscosity of 40.3 seconds (Saybolt Universal) at 210° F., a viscosity index of 101 and containing 12% aromatics as determined by ASTM D-2007. The oil sample remains clear with no separation after being tested at 36° F. overnight and for one week at room temperature. The solution does not corrode copper when tested for three hours at room temperature. When tested for three hours at 212° F. the Oil "A" solution slightly corrodes copper. A solution of 3.65% by weight of the sulfurized oil in Oil "B" is prepared. Oil "B" is a commercial solvent-refined paraffinic base oil having a viscosity of 47.3 seconds (Saybolt Universal) at 210° F., a viscosity index of 103 and containing 13% aromatics as determined by ASTM D-2007. When this 3.65% by weight solution is tested in a standard 4 Ball wear tester under a load of 20 kg. for 60 minutes, at 1800 rpm, at 130° F., 0.48 mm. scars are observed. When this 3.65% by weight solution is subjected to the Falex test using one minute step ups a maximum load of 1750 pounds is obtained. The Falex tests are run on the Falex tester manufactured by the Faville Le Valley Corp., Chicago, Ill., and indicate the extreme pressure lubricity of the composition. In the Falex testing apparatus a ¼ inch diameter steel pin is rotated between two horizontally loaded steel V-blocks. Pressure is applied in 250 pound increments at one minute intervals until the shear pin or the steel pin breaks due to failure of the lubricant film.

EXAMPLE II

Example I is repeated except 120 g. of sulfur are added to the blend of lard oil and $\alpha$-olefin. Ten gram portions of the sulfurized blend are mixed with 100 g. of Oil "A". This mixture does not corrode copper after being tested for 3 hours at room temperature but does after being tested for 3 hours at 212° F. A solution containing 2.96% by weight of the sulfurized blend in Oil "B" is prepared and subjected to the Falex test and the 4 Ball wear test. Using one minute step ups in the Falex test the sample failed at 3500 pounds. In the 4 Ball wear test 0.61 mm. scars were obtained after 60 minutes, under a load of 20 kg. at a speed of 1800 rpm, at 130° C.

EXAMPLE III

Twenty-two hundred and sixty ml. of winter strained lard oil are blended with 400 ml. of tetraisobutylene prepard in accordance with the procedure of Example I of U.S. application Ser. No. 134,095, filed Apr. 14, 1971 by Gary L. Driscoll, in a 5 L kettle equipped with a vibromixer. The mixture is heated to 250° F. and the vibromixer operated at maximum speed. Sulfur (10% by weight) is added and the temperature of the mixture raised to 375° F. for 2 hours. The mixture is then cooled to 230° F. and air is bubbled through the mixture for one hour by means of a glass tube at a moderate rate below that at which splashing and agitation take place. The resulting sulfurized oil is analyzed and found to contain 8.23% sulfur. A ten gram portion of the sulfurized oil is dissolved in 100 g. of Oil "A". The oil sample remains clear with no separation after being tested at 36° F. overnight and for one week at room temperature.

EXAMPLE IV

Winter strained lard oil (2550 ml.) is blended with 450 ml. of triisobutylene prepared in accordance with Example I of United States application Ser. No. 134,095, filed Apr. 14, 1971 by Gary L. Driscoll, in a 5 L kettle equipped with a vibromixer. The mixture is heated to 250° F. and the vibromixer operated at maximum speed. These conditions are maintained while 266 g. of sulfur are added over a period of a few minutes. The temperature is raised to 275° F. for two hours. The mixture is then cooled to 230° F. and air is bubbled through the mixture for one hour by means of a glass tube at a moderate rate below that at which splashing and agitation take place. The resulting sulfurized oil is analyzed and found to contain 8.6% sulfur as based on the total composition. A ten gram portion of the sulfurized oil is dissolved in 100 g. of Oil "A". The Oil sample remains clear with no separation after being tested at 36° F. overnight and for one week at room temperature.

EXAMPLE V

Winter strained lard oil (2550 ml.) is blended with 450 ml. of a commercial blend of $C_{18}$ branched chain olefins containing predominantly mid-chain double bonds in a 5 L kettle equipped with a vibromixer. The mixture is heated to 250° F. and the vibromixer operated at maximum speed. These conditions are maintained while 265 g. of sulfur are added. The temperature is raised to 375° F. for two hours. The mixture is then cooled to 230° F. and air is bubbled through the mixture for one hour by means of a glass tube at a moderate rate below that at which splashing and agitation take place. The resulting sulfurized oil is analyzed and foud to contain 8.58% sulfur. A ten gram portion of the sulfurized oil is dissolved in 100 g. of Oil "A". The oil sample remains clear with no separation after being tested at 36° F. overnight and at room temperature for one week.

EXAMPLE VI

A blend (2646 g.) of 85 vol. % winter strained lard oil and 15 vol. % of a blend of predominantly straight chain α-olefins containing from 15–20 carbon atoms are charged to a 5 L kettle equipped with a vibromixer. The mixture is heated to 300° F. and 530 g. of sulfur are added over a period of 30 minutes. The temperature is raised to 335° F. for 35 minutes. The mixture is then cooled to 212° F. and air is bubbled through the mixture for 17 hours by means of a glass tube at a moderate rate below that at which splashing and agitation take place. The resulting sulfurized oil is analyzed and found to contain 16.33 wt. % sulfur. The sulfurized oil is dissolved in Oil "C" to form a solution containing 28.5% by weight of the sulfurized oil. Oil "C" is a commercial naphthenic base oil having a viscosity of 38.2 seconds (Saybolt Universal) at 210° F., a viscosity index of −10, an average molecular weight of 295, and containing 21% aromatic carbon atoms, 37% naphthenic carbon atoms and 42% paraffinic carbon atoms as determined by ASTM D-2140. Using the Falex one minute step up test a value of 3250 pounds is obtained. In the 4 Ball weld test (Fed. 6503) the weld takes place at 800+ kg. using a 28.5% by weight solution of the sulfurized oil in Oil "C". In the 4 Ball wear test operated for 30 minutes at 1800 rpm, 130° F. and 25 kg. 0.81 mm. scars are observed. Ten grams of the sulfurized oil are dissolved in 100 g. of Oil "A" to form a metal-working oil and is found to remain clear after standing for 16 hours at 36° F. and one week at room temperature. By contrast, both commercial sperm oil and commercial lard oil sulfurized to the same extent separate from solution after the same testing.

EXAMPLE VII

Winter strained lard oil (2550 ml.) is blended with 250 ml. of a blend of predominantly straight chain α-olefins containing from 15 to 20 carbon atoms in a 5 L kettle equipped with a vibromixer. The mixture is heated to 178° F. and 238 g. of sulfur monochloride ($S_2Cl_2$) are added to the blended oils over a period of 15 minutes. At the end of the 15 minutes the temperature has risen to 230° F. The temperature is reduced to 194° F. and air is bubbled through the mixture for 14 hours by means of a glass tube at a moderate rate below that at which splashing and agitation take place. This air blowing serves to remove HCl as well as $H_2S$. The weight loss during this air blowing is 0.17%. The sulfurized oil is analyzed and found to contain 3.96 wt. % sulfur and 3.90 wt. % chlorine.

EXAMPLE VIII

This example illustrates the difference between sulfurizing the lard oil and olefin together and sulfurizing both separately followed by blending and further that this would not be predicted by their solubility in the unsulfurized state.

Fifty vol. % solutions of winter strained lard oil and a blend of 85 vol. % winter strained lard oil and 15 vol. % of the α-olefin used in Examples I, II, VI and VII in Oil "A" are prepared. These solutions exhibited no compatibility differences. Both are clear at room temperature. On cooling to 36° F. both solutions solidify. After warming up to room temperature both solutions regain clarity.

Winter strained lard oil (2699 g.) is charged to a 5 L kettle equipped with a vibromixer. The lard oil is heated to 300° F. and the vibromixer operated at maximum speed. Sulfur (270 g.) is added over a 30 minute period. The temperature is raised to 375° F. and held there for one hour. The temperature is then lowered to 200° F. and air is bubbled through the sulfurized oil for 17 hours at a moderate rate below that at which splashing and agitation take place. The resulting sulfurized lard oil is analyzed and found to contain 8.54 wt. % sulfur.

The $C_{15}$–$C_{20}$ predominantly straight chain α-olefin blend used in Examples I, II, VI and VIII (2356 g.) is charged to a 5 L kettle equipped with a vibromixer. The α-olefin is heated to 300° F. and the vibromixer operated at maximum speed. Sulfur (236 g.) is added over a 30 minute period. The temperature is raised to 335° F. and held there for 30 minutes. Then the temperature is raised to 375° F. and held there for one hour. The temperature is then lowered to 200° F. and air is bubbled through the sulfurized oil for 17 hours at a moderate rate below that at which splashing and agitation take place. The resulting sulfurized α-olefins are analyzed and found to contain 8.99 wt. % sulfur.

The separately sulfurized lard oil and α-olefins are tested for compatibility in Oil "A". When 10 g. of the sulfurized lard oil is disoled in 100 g. of Oil "A" the solution hazes after being tested overnight at 36° F. When 10 g. of the sulfurized α-olefin is dissolved in 100 g. of Oil "A" and tested overnight at 36° F. the solution remains clear with no separation. When 10 g. of an 85:15 percent blend of the sulfurized lard oil and the sulfurized α-olefin are dissolved in 100 g. of Oil "A" and tested overnight at 36° F. the solution hazes. When 10 g. of a 70:30 percent blend of the sulfurized lard oil and the sulfurized α-olefin are dissolved in 100 g. of Oil "A" and tested overnight at 36° F. the solution hazes. Hazing indicates a lack of compatibility between the additive and the paraffinic oil which in use results in the additive forming a sludge and therefore not being available to perform its function. In contrast when sulfurized together the lard oil and α-olefin formed a sulfurized product which is soluble in paraffinic lubricating oils at 36° F.

EXAMPLE IX

This example illustrates the use of an inert gas to remove the $H_2S$ formed during sulfurization.

A blend (2666 g.) of 85 vol. % winter strained lard oil and 15 vol. % of a blend of predominantly straight chain α-olefins containing from 15–20 carbon atoms are charged to a 5 L kettle equipped with a vibromixer operated at maximum speed. These conditions are maintained while 534 g. of sulfur are added over a period of 30 minutes. The temperature is raised to 335° F. for 35 minutes. Nitrogen gas is bubbled through the mixture at a moderate rate below that at which splashing and agitation take place for 2 hours while maintaining the temperature of the mixture at 335° F. The resulting sulfurized oil is analyzed and found to contain 16.19 g. of sulfur.

EXAMPLE X

A blend (2644 g.) of 85 vol. % winter strained lard oil and 15 vol. % of the predominantly straight chain α-olefins containing 15–20 carbon atoms is charged to a 5 L kettle equipped with a vibromixer. The mixture is heated to 250° F. and 264 g. of sulfur are added over a period of a few minutes. The temperature is raised to 375° F. for 2 hours. The mixture is then cooled to 230° F. and air is bubbled through the mixture for 2 hours by means of a glass tube at a moderate rate below that at which splashing and agitation take place. The resulting sulfurized oil is analyzed and found to contain 8.35 wt. % total sulfur and 0.59 wt. % active sulfur.

TABLE II

| Sulfurized Product Example No. | Properties | | | vol. % in SAE 90 Stick/slip ratio |
|---|---|---|---|---|
| | 100% Sulfurized Oil Copper strip | 10 vol. % in Oil "A" | | |
| | | Copper strip | Weld Pt. (kg.) | |
| II | 1 | 1B | 290 | 0.77 |
| IV | 1 | 1B | 260 | 0.84 |
| V | 1 | 1B | 270 | 0.84 |
| VIII (sulfurized lard oil) | 2 | 2C | — | — |
| VIII (sulfurized α-olefin) | 1 | 1B | — | >1.00 |
| X | 1 | 1A | 260 | 0.75 |

In Table II the "copper strip" test is performed in accordance with ASTM D-130. A value below 2 is considered adequate for these materials. The weld point reported in Table II is determined using the standard 4 Ball weld test (Fed. 6503). A value over 250 kg. is considered adequate for a metal-working oil. The stick/slip ratio is the ratio of static friction over dynamic friction. A value below 0.85 is considered adequate for most uses.

EXAMPLES XI TO XXXXI

Examples XI to XXXXI are reported in Tables III and IV. Examples XI to XXXIV illustrate a variety of triglycerides which may be used in the present invention. In each case the solubility of the sulfurized triglyceride in at least one type of paraffinic oil is obtained by consulfurizing the triglyceride with the olefin in the amount indicated in Table III. In each of the examples reported in Table III the olefin used is a blend of predominantly straight chain mono-α-olefins containing from 15 to 20 carbon atoms. All of the solubility data reported in Tables III and IV is based on 10 grams of the sulfurized product in 100 grams of the oil indicated. All of the performance data reported in Tables III and IV is based on a solution of the sulfurized product in Oil "C" (defined above). In each example the sulfurized product is dissolved in Oil "C" in the amount necessary to provide 0.318 wt. % sulfur in the overall composition. The Falex test when performed on Oil "C" without any additive gives a value of less than 250 p.s.i.

In Examples XI to XXIX, XXXV, XXXVI, XXXX and XXXXI the sulfurized product was prepared by charging 500 ml. of the blend indicated of the olefin and triglyceride to a 1000 ml. round bottom glass flask fitted with a thermometer, vibromixer, heating mantle and water cooled reflux condenser. The temperature of the charge was raised to 250° F. and 50 g. of sulfur added over a period of about one minutes. The temperature was raised to 375° F. and held therefor two hours after which the temperature was reduced to 250° F. The temperature was maintained at 250° F. for 2 hours and the sulfurized product air blown for two hours to remove hydrogen sulfide. The product is analyzed for sulfur and this amount is reported in Tables III and IV. In Examples XXX to XXXIV a lard oil-$C_{15}$–$C_{20}$ linear α-olefin blend or the lard oil or olefin as indicated in Table III is sulfurized as above and then the sulfurized product is run through the above-described sequence of steps except sufficient phosphorus sesquisulfide ($P_4S_3$) is added instead of the sulfur to amount to 2 wt. % P in Examples XXX, XXXI and XXXIV and 1 wt. % P in Examples XXXII and XXXIII and a temperature of 220° F. is used for 5 hours. The finished product in Example XXX contained 1.8 wt. % P, in Example XXXI contained 1.5 wt. % P, in Examples XXXII and XXXIII contained 0.86 wt. % P, and in Example XXXIV contained 1.6 wt. % P. In the case of the nominal 2 wt. % P it should be noted that the phosphosulfurized blend is more soluble than either the phosphosulfurized lard oil or the phosphosulfurized olefin. In Examples XXXVII and XXXVIII a bomb reactor is used due to the low boiling points of propylene and hexene. In these examples a 1000 ml. bomb reactor is charged with 500 g. of the lard oil-olefin blend along with 50 g. of sulfur. The bomb is sealed and heated to 375° F. for two hours with agitation. After two hours the product is removed from the bomb, placed in a 1000 ml. round bottom glass flask maintained at 250° F. and air blown for two hours. After this product is complete. In Table III all of the examples use are blend of 85 volume percent lard oil and 15 volume percent of the olefin indicated in the Table.

In Tables III and IV cps stands for centipoises, RT stands for room temperature, LWI stands for load wear index as determined by ASTM D-27-83, OK means the sulfurized product was soluble with no visible haze, S means the sulfurized product separated from the oil, Sl.H means a slight haze was visible and H means a haze was visible. In Tables III and IV Oil "D" is solvent refined bright stock having a viscosity of 169 SUS @ 210° F. V.I. of 95 containing 23% aromatics.

TABLE III

| Example | Triglyceride | Olefin vol. % | Viscosity Charge cps | Viscosity Product cps | Sulfur wt. % | Solubility Oil "A" RT | Oil "A" 36° F. | Oil "A" RT Week | Oil "D" RT | Oil "D" 36° F. | Oil "D" RT Week | Falex psi | Stick Slip | Performance Wear mm | Weld psi | LWI |
|---|---|---|---|---|---|---|---|---|---|---|---|---|---|---|---|---|
| XI | Lard Oil | 0 | 55 | 3760 | 8.98 | OK | H | OK | H | H | H | 1250 | 0.83 | 0.46 | 200 | 25.4 |
| XII | Lard Oil | 15 | 33.5 | 1100 | 9.56 | OK | OK | OK | OK | Sl.H | Sl.H | 1000 | 0.74 | 0.46 | 200 | 25.9 |
| XIII | Lard Oil | 25 | 20.0 | 610 | 9.23 | OK | OK | OK | OK | OK | OK | 750 | | | | |
| XIV | Soybean Oil | 0 | 44 | 3850 | 9.46 | S | S | S | S | S | S | | >1 | | | 21.8 |
| XV | Soybean Oil | 15 | 29 | 1680 | 9.41 | OK | OK | OK | H | H | H | 1000 | 0.82 | 0.53 | 200 | 25.4 |
| XVI | Soybean Oil | 25 | 22.5 | 1000 | 9.48 | OK | OK | OK | H | H | H | 750 | 0.85 | 0.53 | 200 | 21.4 |
| XVIII | Soybean Oil | 30 | 19.5 | 725 | 9.09 | OK | OK | OK | H | H | H | 500 | 0.86 | 0.52 | 200 | 20.3 |
| XIX | Soybean Oil | 50 | 13 | 268 | | OK | OK | OK | OK | OK | OK | 750 | | 0.50 | 200 | |
| XX | Cottonseed Oil | 25 | 24 | 640 | 9.27 | OK | OK | OK | H | H | H | 1000 | 0.83 | 0.51 | 200 | 21.2 |
| XXI | Cottonseed Oil | 50 | 14 | 275 | 9.4 | OK | OK | OK | OK | OK | OK | | | | | |
| XXII | Sunflower Oil | 15 | 28 | 2120 | 8.78 | OK | OK | OK | H | H | H | 750 | 0.84 | 0.57 | 200 | 25.1 |
| XXIII | Sunflower Oil | 25 | 24.5 | 550 | 7.45 | OK | H | OK | Tr | Tr | Tr | 750 | 0.87 | 0.44 | 200 | 25.0 |
| XXIV | Safflower Oil | 25 | 23 | 1820 | 9.69 | OK | OK | OK | H | H | H | 750 | 0.83 | 0.47 | 250 | 24.0 |
| XXV | Peanut Oil | 25 | 26 | 950 | 9.37 | OK | OK | OK | H | OK | OK | 750 | 0.86 | 0.49 | 200 | 21.3 |
| XXVI | Menhaden Oil | 25 | 20 | 770 | 7.45 | OK | OK | OK | H | H | H | | | | | |
| XXVII | Tall Oil (4% rosin) | 0 | 28 | 460 | 9.22 | H | H | S | H | H | S | | | | | |
| XXIX | Tall Oil (4% rosin) | 25 | 17 | 260 | 9.22 | H | H | H | H | H | H | 1250 | 0.73 | 0.43 | 160 | 23.1 |
| XXX | Tall Oil (25% rosin) | 25 | 27.5 | 970 | 9.18 | Sl.H | Sl.H | OK | Sl.H | Sl.H | Sl.H | 750 | 0.73 | 0.44 | 160 | 23.0 |
| XXXI | Lard Oil (2% P) | 0 | | | 9.5 | Sl.H | H | | H | H | | 2500 | 0.84 | 0.44 | 315 | 30.4 |
| XXXII | Lard Oil (2% P) | 15 | | | 8.4 | S | S. | | S | S | 2250 | 0.74 | 0.45 | 200 | 30.2 | |
| XXXIII | Lard Oil (1% P) | 0 | | | 8.59 | OK | OK | | OK | OK | | | | | | |
| XXXIV | Lard Oil (1%) 2% P | 15 / 100 | | | 8.97 / 10 | Sl.H | H | OK | OK | Sl.H | | 1000 | 0.93 | 0.41 | 160 | 19.0 |

TABLE IV

| Example | Olefin | Viscosity Charge cps | Viscosity Product cps | Sulfur wt. % | Solubility Oil "A" RT | Oil "A" 36° F. | Oil "A" RT Week | Oil "D" RT | Oil "D" 36° F. | Oil "D" RT Week | Performance Falex psi | Stick Slip | Wear mm | Weld psi | LWI |
|---|---|---|---|---|---|---|---|---|---|---|---|---|---|---|---|
| XXXV | C$_{15}$–C$_{20}$ Linear α-olefin | 33.5 | 1100 | 8.98 | OK | OK | OK | OK | H | H | 1250 | 0.83 | 0.46 | 200 | 25.4 |
| XXXVI | 1-decene | 27 | 760 | 9.64 | OK | OK | OK | OK | OK | OK | 1250 | 0.79 | 0.45 | 200 | 30.2 |
| XXXVII | 1-hexene | | 960 | 10.95 | OK | OK | OK | OK | Sl. H | Sl. H | 1000 | 0.84 | 0.46 | 20 | 25.9 |
| XXXVIII | Propylene | | 375 | 7.37 | OK | H | OK | OK | OK | OK | 1250 | 0.82 | 0.52 | 200 | 21.9 |
| XXXIX | cyclo dodecene | 36 | 1240 | 9.09 | OK | OK | Sl. H | Sl.H | H | Sl. H | 1250 | 0.79 | 0.45 | 200 | 30.2 |
| XXXX | styrene | 19 | 930 | 9.16 | OK | OK | OK | Sl. H | H | H | 750 | 0.81 | 0.46 | 200 | 22.6 |
| XXXXI | 1-phenyl-2-butene | 23 | 690 | 8.88 | OK | OK | Sl. H | Sl.H | H | H | 750 | 0.81 | 0.47 | 200 | 25.0 |

The invention claimed is:

1. A composition comprising a consulfurized blend of 50 to 90 parts by volume o a triglyceride wherein the fatty acid moieties of said triglyceride contain principally from 9 to 22 carbon atoms and at least about 45 mole percent of the fatty acid moieties present contain one ethylenically unsaturated carbon-carbon double bond and wherein said fatty acid moieties are hydrocarbons except for the carboxylic group of said fatty acid moieties, and from 50 to 10 parts by volume of a hydrocarbon containing from 2 to about 24 carbon atoms and having the structure

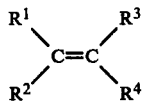

wherein R$^1$, R$^2$ and R$^3$ are either hydrogen or alkyl and R$^4$ is either hydrogen, alkyl, aryl, cycloalkyl or alkaryl, which consulfurized blend contains chemically combined therewith from 16 to 25 weight percent as based on said blend of sulfur of which from 5 to 18 weight percent is active sulfur.

2. The composition of claim 1 wherein R$^4$ is alkyl.

3. The composition of claim 2 wherein the triglyceride is lard oil.

4. The composition of claim 3 wherein R$^1$, R$^2$ and R$^3$ are hydrogen.

5. The composition of claim 4 wherein from 88 to 70 parts by volume of lard oil and from 12 to 30 parts by volume of hydrocarbon are cosulfurized in said blend.

6. A composition comprising a consulfurized blend of from 50 to 90 parts by volume of a triglyceride wherein the fatty acid moieties of said triglyceride contain principally from 9 to 22 carbon atoms and at least about 45 mole percent of the fatty acid moieties present contain one ethylenically unsaturated carbon-carbon double bond and wherein said fatty acid moieties are hydrocarbons except for the carboxylic group of said fatty acid moieties, and from 50 to 10 parts by volume of a hydrocarbon containing from 2 to about 24 carbon atoms and having the structure

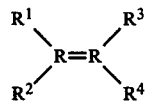

wherein R$^1$, R$^2$ and R$^3$ are either hydrogen or alkyl and R$^4$ is either hydrogen, alkyl, aryl, cycloalkyl or alkaryl, which consulfurized blend contains chemically combined therewith from 7.5 to 25 wt. % as based on said blend of sulfur.

7. The composition of claim 6 wherein the cosulfurized blend contains from 7.5 to 11 wt. % as based on the blend of sulfur which composition contains less than 2.5 wt. % active sulfur.

8. The composition of claim 7 wherein the triglyceride is lard oil.

9. The composition of claim 8 wherein R$^4$ is alkyl.

10. The composition of claim 9 wherein R$^1$, R$^2$ and R$^3$ are hydrogen.

11. The composition of claim 6 wherein from 88 to 70 parts by volume of triglyceride and from 12 to 30 parts by volume of the hydrocarbon are used.

12. The composition of claim 11 wherein R$^4$ is alkyl.

13. The composition of claim 12 wherein R$^1$, R$^2$ and R$^3$ are hydrogen.

14. The composition of claim 13 wherein the triglyceride is lard oil.

15. A composition comprising a consulfurized blend of from 88 to 70 parts by volume of lard oil and from 12 to 30 parts by volume of straight chain-α-olefins containing from 15 to 20 carbon atoms, which co-sulfurized blend contains chemically combined therewith from 7.5 to 25 wt. % as based on said blend of sulfur.

* * * * *

UNITED STATES PATENT OFFICE
CERTIFICATE OF CORRECTION

PATENT NO. : 4,166,796
DATED : September 4, 1979
INVENTOR(S) : ALEXANDER D. RECCHUITE It is certified that error appears in the above-identified patent and that said Letters Patent are hereby corrected as shown below:

In the Title, the words "LARD OIL" should read ---TRIGLYCERIDE---.

The word "consulfurized" should read ---cosulfurized--- in each of the following occurrences:

Claim 1:  Column 13, line 18 and line 38

Claim 6:  Column 13, line 49
          Column 14, line 29

Claim 15: Column 14, line 50

In Claim 1: Column 13, line 19; "o" should read ---of---.

Signed and Sealed this

Eleventh Day of December 1979

[SEAL]

Attest:

SIDNEY A. DIAMOND

Attesting Officer

Commissioner of Patents and Trademarks